(12) United States Patent
Lee et al.

(10) Patent No.: US 8,203,455 B2
(45) Date of Patent: Jun. 19, 2012

(54) POSTURE SENSING ALERT APPARATUS

(76) Inventors: Kun-Ta Lee, Taipei Hsien (TW); Chih Lo, Taipei Hsien (TW); Ching-Yen Lee, Taipei Hsien (TW); Ching-Hua Lee, Taipei Hsien (TW); Ching-Jung Lee, Taipei Hsien (TW)

( * ) Notice: Subject to any disclaimer, the term of this patent is extended or adjusted under 35 U.S.C. 154(b) by 379 days.

(21) Appl. No.: 12/473,375

(22) Filed: May 28, 2009

(65) Prior Publication Data

US 2010/0109880 A1    May 6, 2010

(30) Foreign Application Priority Data

Oct. 31, 2008  (TW) .............................. 97142016 A

(51) Int. Cl.
*G08B 23/00*    (2006.01)

(52) U.S. Cl. ............... 340/573.7; 340/573.4; 340/568.2; 340/566; 340/665; 340/568.4; 600/544; 600/547; 600/345; 600/347; 600/365; 600/485

(58) Field of Classification Search .............. 340/573.7, 340/573.4, 568.2, 566, 665, 568.4; 600/544, 600/547, 345, 347, 365, 485
See application file for complete search history.

(56) References Cited

U.S. PATENT DOCUMENTS

| 5,107,826 | A  | * | 4/1992  | Andersson    | 602/19  |
|-----------|----|---|---------|--------------|---------|
| 6,554,781 | B1 |   | 4/2003  | Carter et al.|         |
| 6,827,694 | B2 | * | 12/2004 | Gladoun      | 600/594 |
| 7,698,830 | B2 | * | 4/2010  | Townsend et al. | 33/512 |
| 7,771,318 | B2 | * | 8/2010  | Narayanaswami | 482/8  |

FOREIGN PATENT DOCUMENTS

| JP | 1982-025847 A | 2/1982  |
| JP | 2002-532125 A | 10/2002 |

OTHER PUBLICATIONS

English language translation of abstract of JP 1982-025847.
Japanese Office Action mailed Feb. 21, 2012.
Machine translation of Japanese Office Action mailed Feb. 21, 2012.

* cited by examiner

*Primary Examiner* — Tai T Nguyen
(74) *Attorney, Agent, or Firm* — Thomas, Kayden, Horstemeyer & Risley, LLP

(57) ABSTRACT

A posture sensing alert apparatus is provided. The posture sensing alert apparatus comprises an attachment element, a detecting element, a processing element and an alert element. The attachment element is adapted to attach on a human body. The detecting element is disposed on the attachment element and is adapted to sense a posture change from the human body. The processing element is disposed on the attachment element and connects to the detecting element. The processing element is adapted to output a signal to the alert element in response to the posture change for a predetermined period so that the alert element is adapted to output an alert accordingly.

19 Claims, 7 Drawing Sheets

POSTURE SENSING ALERT APPARATUS

This application claims priority to Taiwan Patent Application No. 097142016 filed on Oct. 31, 2008.

CROSS-REFERENCES TO RELATED APPLICATIONS

Not applicable.

BACKGROUND OF THE INVENTION

1. Field of the Invention

The present invention relates to an alert apparatus, and particularly, to a posture sensing alert apparatus for preventing bad postures of the human body.

2. Descriptions of the Related Art

It is often the case that people have bad postures because they pay little attention to their sitting postures or stances. It is especially hard for people to perceive their own bad postures because they have been accustomed to such postures. Consequently, such bad postures tend to affect the body's health by causing a hunchback after an extended period of time. Currently, a variety of products for preventing hunchbacks and keeping proper postures can be found in the market, such as posture-correcting bands, posture-correcting waistbands and hunchback-preventing desks and chairs. However, such products are mostly able to only adjust the postures but unable to alert the user of bad posture. Moreover, such products are disadvantageous in that they are very bulky and inconvenient to store and carry, so it is difficult for users to keep standard postures at all times.

In view of these drawbacks of the prior art, it is highly desirable in the art to develop a posture sensing alert apparatus with a small volume, comfortable to use and capable of giving an alert signal.

SUMMARY OF THE INVENTION

The objective of this invention is to provide a posture sensing alert apparatus capable of preventing bad postures to overcome the drawbacks of the prior art. When attached on a user's body, the posture sensing alert apparatus can actively warn the user of his bad posture for timely correction.

To this end, the present invention discloses a posture sensing alert apparatus, which comprises an attachment element, a detecting element, a processing element, and an alert element. The attachment element is adapted to be attached on a human body. The detecting element is disposed on the attachment element to sense a strain from the human body. The processing element is disposed on the attachment element and connected to the detecting element, and is adapted to output a sensing signal in response to the strain. The alert element is disposed on the attachment element and connected to the processing element, and is adapted to output an alert signal in response to the sensing signal.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

FIG. 5b is a schematic partially enlarged view of FIG. 5a.

DESCRIPTION OF THE PREFERRED EMBODIMENT

Figure 1:
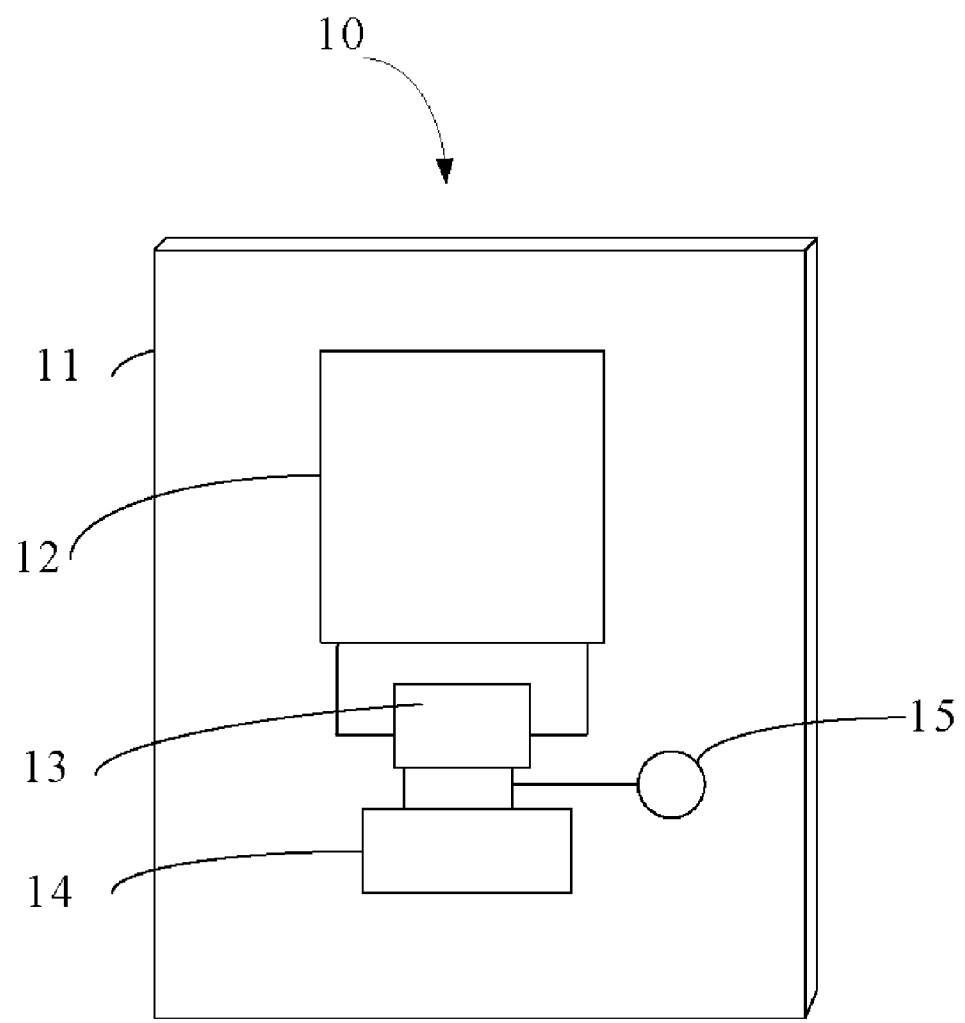
FIG. 1 is a schematic view of an embodiment of a posture sensing alert apparatus of the present invention.
Figure 2:
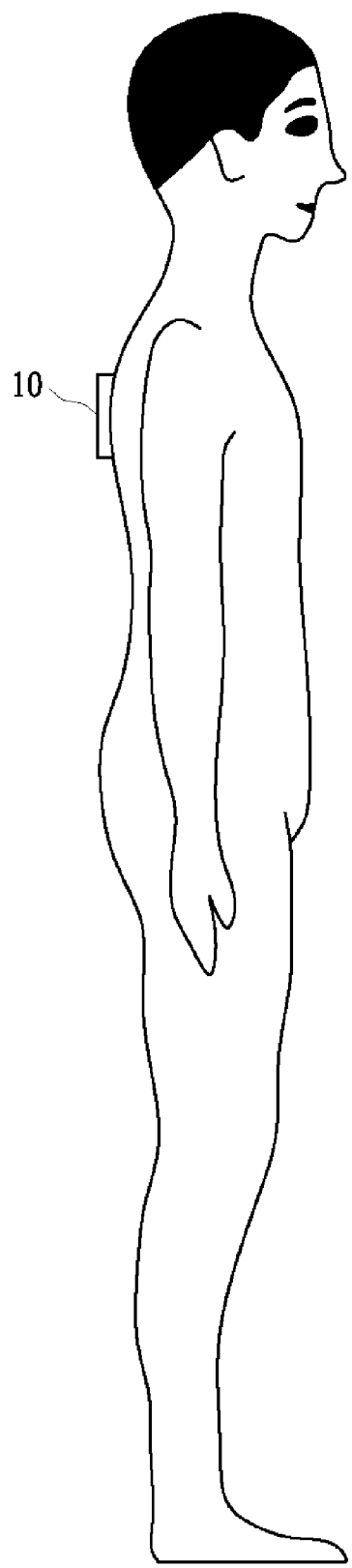
FIG. 2 is a schematic view illustrating the posture sensing alert apparatus of the present invention attached on a human body's back.

FIG. 1 is a schematic view of an embodiment of a posture sensing alert apparatus according to the present invention. The posture sensing alert apparatus 10 comprises an attachment element 11, a detecting element 12, a processing element 13, an alert element 14 and an electric power source 15. As will be appreciated, the present invention is characterized in that the attachment element 11 is preferably a soft patch adapted to be completely attached on a human body to detect the human body's postures in real time for monitoring purposes. As shown in FIG. 2, there is a schematic view illustrating the attachment element 11 attached on the human body's back. In this embodiment, the electric power source 15 is electrically connected to the detecting element 12, the processing element 13 and the alert element 14 to supply electric power required by these elements.

Figure 3:
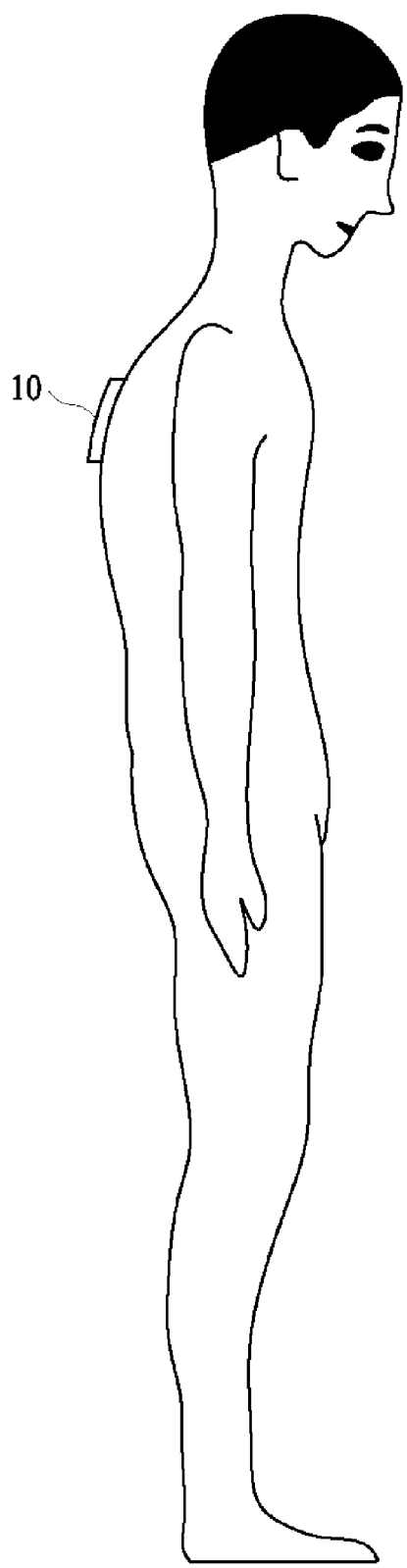
FIG. 3 is a schematic view illustrates the posture sensing alert apparatus of the present invention that senses bad body posture.

On the other hand, the detecting element 12 is disposed on the attachment element 11 to sense a strain resulting from a change in the posture of the human body. As shown in FIG. 3, when the user hunches his or her back, a strain resulting from the human body's hunching action is sensed by the detecting element 12. Specifically, the detecting element 12 may have several implementations, which will be detailed hereinafter. The processing unit 13 is disposed on the attachment element 11 and connected to the detecting element 12 so that it can output a sensing signal (not shown) to the alert element 14 in response to the strain after a predetermined period. For example, if the detecting element 12 continuously detects a strain resulting from a change in the posture of the human body, the processing element 13 can output a sensing signal to the alert 14 after the predetermined period (e.g., tens of seconds) so that the alert element 14 will output an alert signal (not shown). In the preferred example, the time length of the predetermined period may be adjusted depending on the user's needs; for example, when the user has kept a bad posture continuously for 30 seconds, the processing element 13 will send a sensing signal to the alert element 14 so that the alert element 14 outputs an alert signal to warn the user of the bad posture.

In this embodiment, the alert element 14 is disposed on the attachment element 11 and is connected to the processing element 13 to output the alert signal in response to the sensing signal. Specifically, the alert element 14 may also be separately hung on the user's body or objects other than the user independently from the attachment element 11. As an example, if the attachment element 11 is attached on a toddler, the alert element 14 may be hung at a location near his or her parent so that the parent will be informed that the toddler is now having a bad posture.

Figure 4:
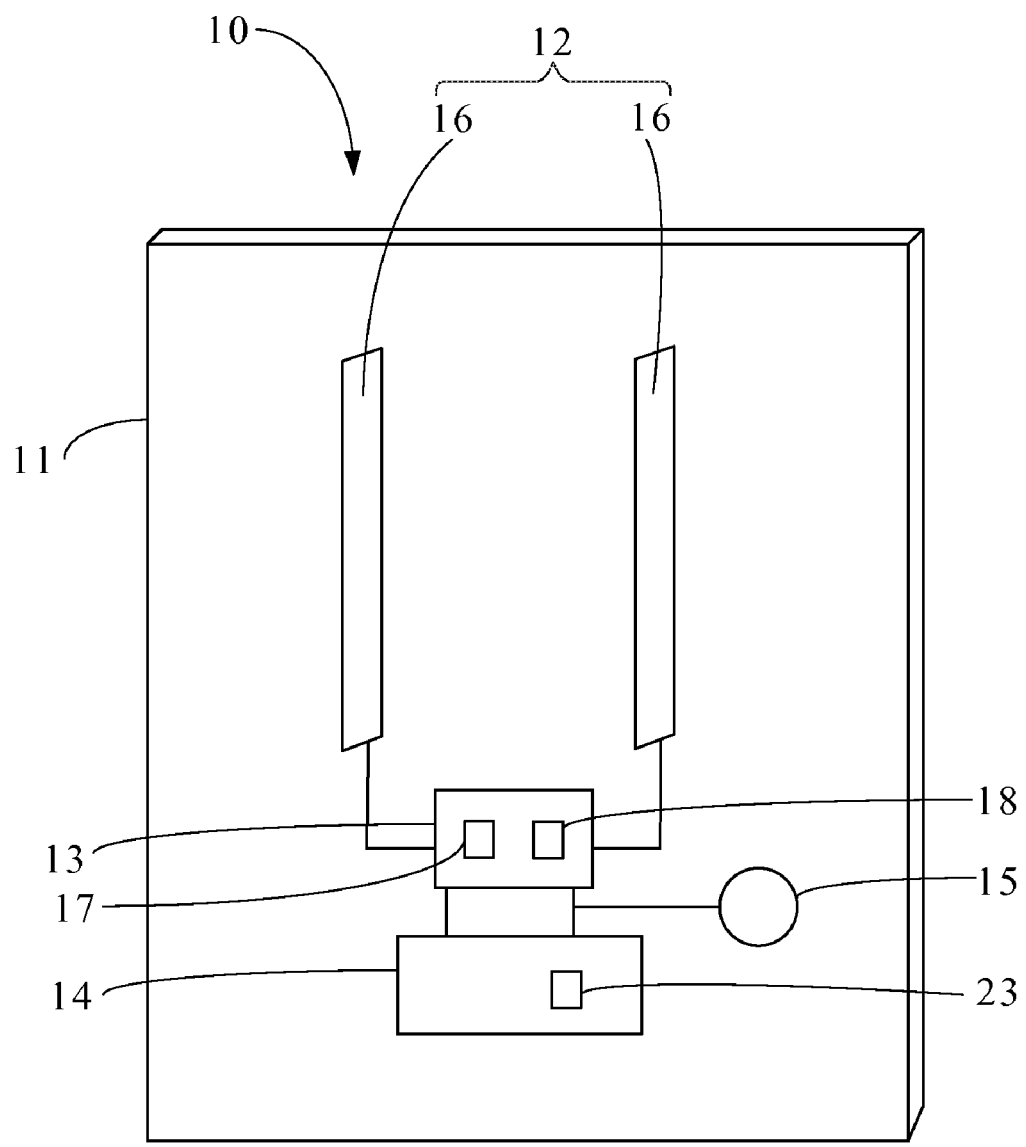
FIG. 4 is a schematic view of an embodiment of the posture sensing alert apparatus of the present invention.

The following descriptions are directed to several examples of the detecting element in the posture sensing alert apparatus of the present invention, where other elements are substantially identical or similar to those described above. In reference to FIG. 4, the detecting element 12 of the posture sensing alert apparatus 10 comprises a piezoelectric patch 16, which works on the following principle: a strain resulting from a change in posture of the human body will alter a resistance of the piezoelectric patch 16. For example, the piezoelectric patch 16 applied in the present invention may be designed with different structures depending on different specifications, e.g., (1) the tube type, (2) the stacked type, (3) the laminar type or (4) the bimorph type, although it is not merely limited thereto.

In more detail, when subjected to a strain, the piezoelectric patch 16 will exhibit a tiny change in resistance. To analyze the tiny change, the processing element 13 comprises a microprocessor 17, which is electrically connected to the piezoelectric patch 16 to generate a sensing signal in response to the change in resistance of the piezoelectric patch 16. The processing element 13 should further comprise a timer 18 adapted to calculate a period of the resistance change of the piezoelectric patch 16. The microprocessor 17 will output the sensing signal only when this period exceeds a predetermined period stored in the timer.

On the other hand, in this embodiment, the detecting element 12 and the processing element 13 may be integrated into a system on chip (SOC) to integrate circuits of different functions. This may reduce the volume of the posture sensing alerting apparatus 10 for convenience in use.

Figure 5A:
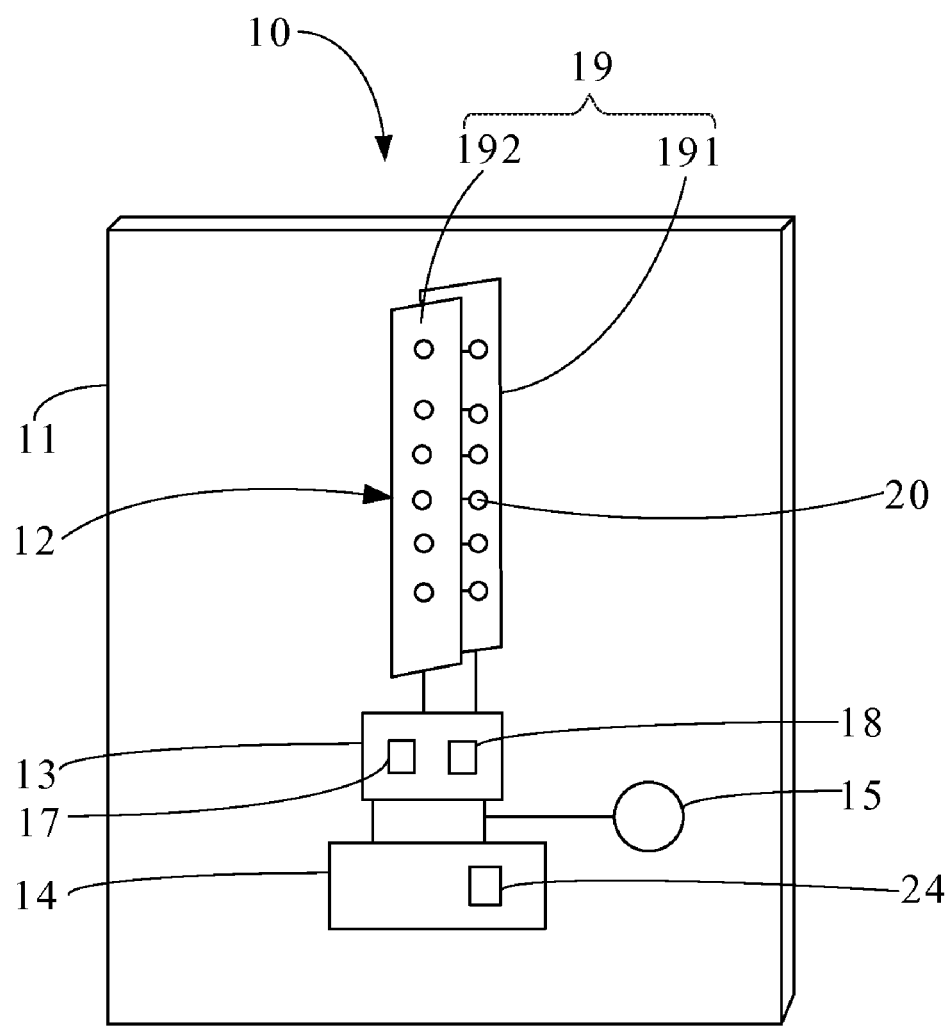
FIG. 5a is a schematic view of another embodiment of the posture sensing alert apparatus of the present invention.
Figure 5B:
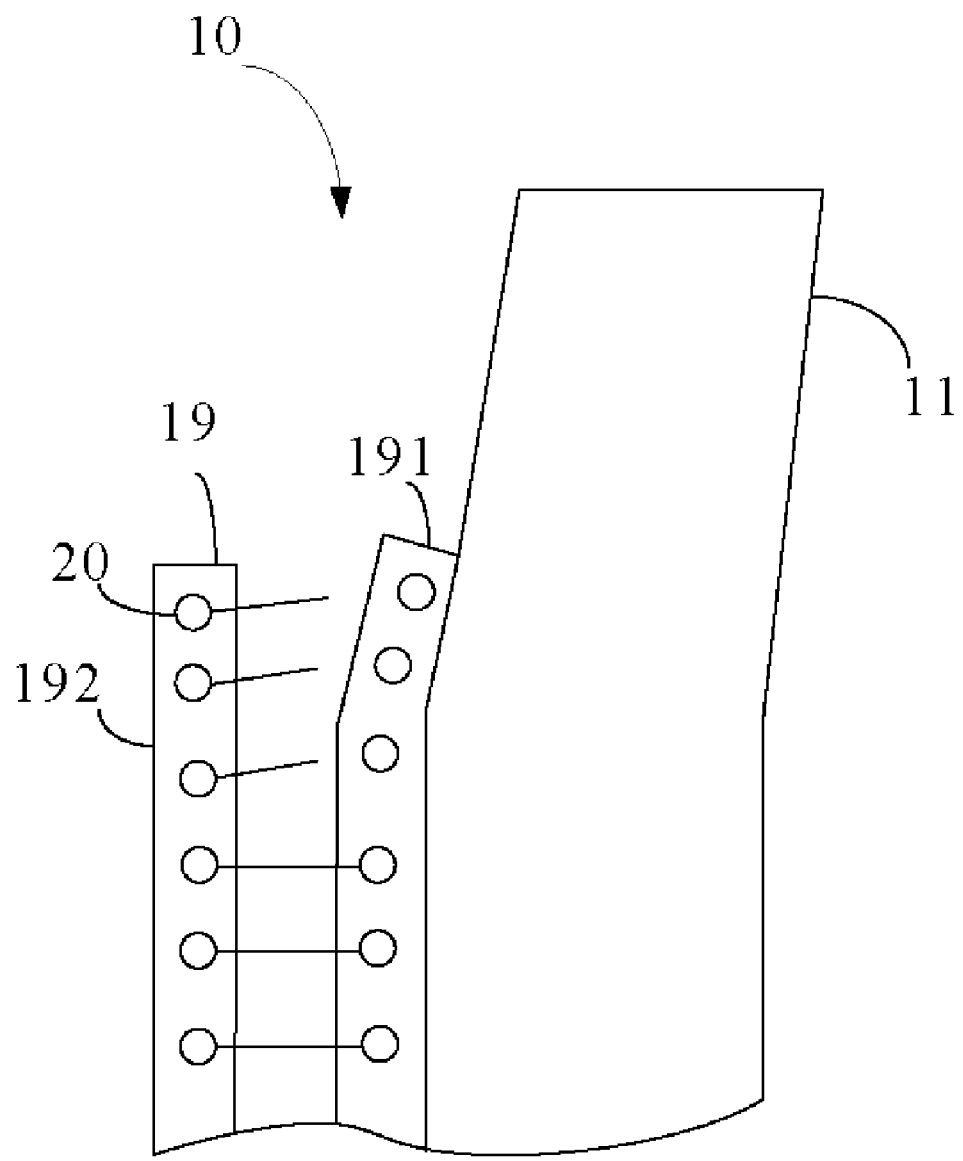

FIG. 5a is another embodiment of the posture sensing alert apparatus of the present invention. In the posture sensing alert apparatus 10 of this embodiment, the detecting element 12 is made of a dual metal sheet 19. In more detail, the dual metal sheet 19 is comprised of two pieces of metal in combination, one of which 191 is attached tightly to the attachment element 11 and the other 192 is joined with the metal piece 191 by means of a plurality of connecting points 20 connected to each other. FIG. 5b is a schematic partial view of FIG. 5a. When the human body changes its posture, a resulting strain will lead to the separation of the connecting points 20 from each other in sequence between the two pieces of metal, resulting in a change of the total resistance value of the dual metal sheet 19. In response to the change in resistance of the dual metal sheet 19, the detecting element 12 generates a sensing signal in order for the alert element to generate an alert signal. Details of the elements and operations thereof in this embodiment are generally the same as those of the previous embodiments and, thus, will not be further described herein.

Figure 6:
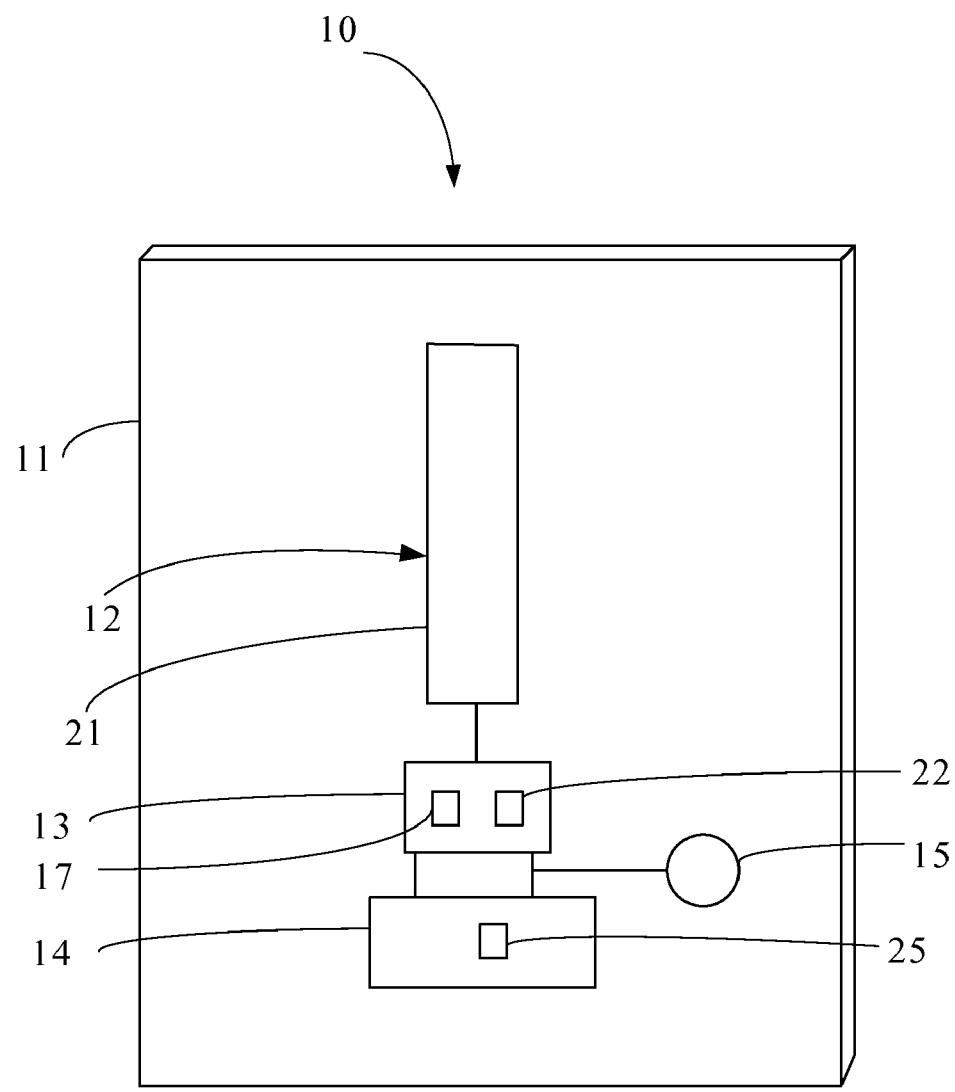
FIG. 6 is a schematic view of a further embodiment of the posture sensing alert apparatus of the present invention.

FIG. 6 is a further embodiment of the posture sensing alert apparatus of the present invention. In this embodiment, the detecting element 12 comprises an elastic hydraulic rod 21 with a variable volume whose volume and internal pressure change in response to the strain caused by the posture of the human body. In this embodiment, the processing element 13 comprises a switch 22 connected to the elastic hydraulic rod 21, which is adapted to output a sensing signal in response to a change in the volume of the elastic hydraulic rod 21 in order for the alert element to generate an alert signal. Details of the elements and operations thereof in this embodiment are generally the same as those of the previous embodiments and, thus, will not be further described herein.

The alert element 14 in the posture sensing alert apparatus 10 of the present invention also has a number of implementations, which will be described respectively hereinbelow, although the alert element 14 is not limited thereto. The aforesaid different examples of the detecting element 12 may also be used in conjunction with the following different examples of the alert element 14 for alerting purposes. In reference to FIG. 4, the alert element 14 illustrated therein comprises a motor 23 adapted to output a vibration signal as the alert signal. In this embodiment, the motor 23 may be a mini-motor generally with a maximum dimension ranging from 3 mm to 10 mm to maintain a smaller size. Another example is shown in FIG. 5a, where the alert element 14 comprises a buzzer 24 capable of outputting a beep tone as the alert signal. Additionally, the alert element 14 shown in FIG. 6 comprises a radio frequency generator 25, the alert signal outputted by which is an electric current signal, for example, a low frequency electric current signal. The low frequency electric current signal can irritate the user's nerves, acupoints or muscles for alerting purposes. Generally, this low frequency electric current signal has a voltage of higher than 600 V but a small current value, i.e., only about several amperes, so it is harmless to the human body.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A posture sensing alert apparatus comprising:
   an attachment element, being adapted to be attached on a human body;
   a detecting element, being disposed on the attachment element to sense a strain from the human body, the detecting element comprising a dual metal sheet and a resistance change of the dual metal sheet will be generated in response to the strain;
   a processing element, being disposed on the attachment element and connected to the detecting element and being adapted to output a sensing signal in response to the strain after a predetermined period; and
   an alert element, being adapted to output an alert signal in response to the sensing signal.

2. The posture sensing alert apparatus as claimed in claim 1, wherein the processing element comprises a microprocessor, electrically connected to the dual metal sheet and the microprocessor is adapted to output the sensing signal in response to the resistance change of the dual metal sheet.

3. The posture sensing alert apparatus as claimed in claim 2, wherein the processing element further comprises a timer, adapted to compute a period of the resistance change of the dual metal sheet, and when the period is over the predetermined period, the microprocessor outputs the sensing signal.

4. The posture sensing alert apparatus as claimed in claim 1, wherein the dual metal sheet comprises a plurality of connecting points connected to each other and the connecting points are adapted to be separated in sequence in response to the strain.

5. The posture sensing alert apparatus as claimed in claim 1, wherein the alert element comprises a motor and the alert signal outputted by the motor is a vibration signal.

6. The posture sensing alert apparatus as claimed in claim 1, wherein the alert element comprises a buzzer and the alert signal outputted by the buzzer is a beep tone.

7. The posture sensing alert apparatus as claimed in claim 1, wherein the alert element comprises a radio frequency generator and the alert signal outputted by the radio frequency generator is an electric current signal.

8. The posture sensing alert apparatus as claimed in claim 1, further comprising an electric source electrically connected to the processing element and the alert element.

9. The posture sensing alert apparatus as claimed in claim 1, where the attachment element is a soft patch completely attached on the human body.

10. The posture sensing alert apparatus as claimed in claim 1, where the predetermined period is adjustable.

11. A posture sensing alert apparatus comprising:
- an attachment element, being adapted to be attached on a human body;
- a detecting element, being disposed on the attachment element to sense a strain from the human body, the detecting element comprising an elastic hydraulic rod, and a volume change of the elastic hydraulic rod will be generated in response to the strain;
- a processing element, being disposed on the attachment element and connected to the detecting element and being adapted to output a sensing signal in response to the strain after a predetermined period; and
- an alert element, being adapted to output an alert signal in response to the sensing signal.

12. The posture sensing alert apparatus as claimed in claim 11, wherein the processing element comprises a switch connected to the elastic hydraulic rod and the volume change of the elastic hydraulic rod will be generated in response to the sensing signal.

13. The posture sensing alert apparatus as claimed in claim 12, wherein the processing element further comprises a timer, adapted to compute a period of the volume change of the elastic hydraulic rod, and when the period is over the predetermined period, the switch outputs the sensing signal.

14. The posture sensing alert apparatus as claimed in claim 11, wherein the alert element comprises a motor and the alert signal outputted by the motor is a vibration signal.

15. The posture sensing alert apparatus as claimed in claim 11, wherein the alert element comprises a buzzer and the alert signal outputted by the buzzer is a beep tone.

16. The posture sensing alert apparatus as claimed in claim 11, wherein the alert element comprises a radio frequency generator and the alert signal outputted by the radio frequency generator is an electric current signal.

17. The posture sensing alert apparatus as claimed in claim 11, further comprising an electric source electrically connected to the processing element and the alert element.

18. The posture sensing alert apparatus as claimed in claim 11, where the attachment element is a soft patch completely attached on the human body.

19. The posture sensing alert apparatus as claimed in claim 11, where the predetermined period is adjustable.

* * * * *